(12) United States Patent
Missling (10) Patent No.: US 11,337,953 B2
(45) Date of Patent: May 24, 2022

(54) A2-73 AS A THERAPEUTIC FOR INSOMNIA, ANXIETY, AND AGITATION

(71) Applicant: ANAVEX LIFE SCIENCES CORP., New York, NY (US)

(72) Inventor: Christopher U. Missling, New York, NY (US)

(73) Assignee: ANAVEX LIFE SCIENCES CORP., New York, NY (US)

( * ) Notice: Subject to any disclaimer, the term of this patent is extended or adjusted under 35 U.S.C. 154(b) by 415 days.

(21) Appl. No.: 16/323,457

(22) PCT Filed: Jul. 27, 2017

(86) PCT No.: PCT/US2017/044111
§ 371 (c)(1),
(2) Date: Feb. 5, 2019

(87) PCT Pub. No.: WO2018/022848
PCT Pub. Date: Feb. 1, 2018

(65) Prior Publication Data
US 2021/0085637 A1   Mar. 25, 2021

Related U.S. Application Data (60) Provisional application No. 62/367,253, filed on Jul. 27, 2016.

(51) Int. Cl.
*A61K 31/341*     (2006.01)
*A61P 25/28*      (2006.01)
*A61K 9/00*       (2006.01)

(52) U.S. Cl.
CPC .......... *A61K 31/341* (2013.01); *A61K 9/0053* (2013.01); *A61P 25/28* (2018.01)

(58) Field of Classification Search
CPC .................................................. A61K 31/341
See application file for complete search history.

(56) References Cited

U.S. PATENT DOCUMENTS 9,750,746 B2 *   9/2017   Vamvakides .......... A61K 31/13
10,813,907 B2 * 10/2020   Missling ................ A61K 31/55
2011/0021552 A1  1/2011   Berg
2016/0022653 A1  1/2016   Dooley

FOREIGN PATENT DOCUMENTS

WO   2017132127 A1   8/2017

OTHER PUBLICATIONS

International Search Report and Written Opinion dated Oct. 6, 2017 in corresponding International Patent Application No. PCT/US2017/044111.
Anavex Life Sciences Corp., Anavex Announces Two-Year Clinical Extension Studyof Anavex 2-73 and Presents Phase 2a Dose-Response Analysis at AAT Conference, Press Release, Mar. 10, 2016 [retrieved from the internet on Sep. 14, 2017—URL: http://www.anavex.com/anavex-announces-two-year-clinical-extension-study-of-anavex-2-73-and-presents-phase-2a-dose-response-analysis-at-aat-conference/.
Extended European Search Report dated Mar. 16, 2020 in corresponding European Patent Application No. 17835251.4.

* cited by examiner

*Primary Examiner* — Golam M Shameem
(74) *Attorney, Agent, or Firm* — Polsinelli PC; Tara A. Nealey; Rong Yang (57) ABSTRACT

A2-73 is a useful therapeutic in the treatment of humans suffering from insomnia, anxiety or agitation. Particular attention is made to oral daily doses of from about 10 mg to about 50 mg, with particular reference to about 20 to 30 mg.

10 Claims, 5 Drawing Sheets

A2-73 AS A THERAPEUTIC FOR INSOMNIA, ANXIETY, AND AGITATION

FIELD OF THE INVENTION

A2-73 is a useful therapeutic in the treatment of humans suffering from insomnia, anxiety or agitation. Particular attention is made to oral daily doses of from about 10 mg to about 50 mg, with particular reference to about 20 to 30 mg, but further including does of up to about 100 mg per day. Attention is also directed to A1-41 and A19-144 as similarly useful therapeutics in insomnia, anxiety or agitation. Also presented is a method of moderating systolic blood pressure.

BACKGROUND OF THE INVENTION

Sleep fragmentation, decreased REM and slow-wave sleep (SWS) and circadian rhythm dysfunction are hallmarks of Alzheimer's disease (AD), causing substantial distress for both patients and their caregivers, and contributing to early institutionalization. Sleep disturbances are among the earliest signs of cognitive decline and may accelerate disease progression but there is a distinct lack of evidence to help guide drug treatment. Recent work supports a role for sleep in the development of AD by influencing amyloid beta (Aβ) physiology. Aβ reportedly fluctuates with the sleep-wake cycle with Aβ levels being higher during wakefulness and lower during sleep. Relatedly, sleep deprivation in transgenic mice accelerates Aβ deposition, whereas improvement of sleep decreases it. Amyloid deposition further disrupts sleep, potentially through increased astrocytosis.

Insomnia can be grouped into primary and secondary insomnia. Primary insomnia is a sleep disorder not due to a medical, psychiatric, or environmental cause. It is described as a complaint of prolonged sleep onset latency, disturbance of sleep maintenance, or the experience of non-refreshing sleep. Conditions that reportedly result in insomnia include depression, pain, benign prostatic hypertrophy, obstructive sleep apnea, restless leg syndrome, and substance misuse. A diagnosis will differentiate between primary insomnia, insomnia as secondary to another condition, and primary insomnia co-morbid with one or more conditions.

Agitation often accompanies dementia and often precedes the diagnosis of common age-related disorders of cognition such as Alzheimer's disease. More than 80% of people who develop AD eventually become agitated or aggressive.

Occasional anxiety is a normal part of life. Anxiety disorders are characterized by frequent intense, excessive and persistent worry and fear about everyday situations. The disorders often involve repeated episodes of sudden feelings of intense anxiety and fear or terror that reach a peak within minutes (panic attacks).

Reference is made to 1-(2,2-diphenyltetrahydrofuran-3-yl)-N-methylmethanamine hydrochloride (ANAVEX™19-144, or A19-144). A19-144 is a compound which is believed to bind to muscarinic acetylcholine and sigma-1 receptors with affinities in the low micromolar range. A19-144 functions similarly to A2-73. Reference is similarly made to tetrahydro-N,N-dimethyl-5,5-diphenyl-3-furanmethanamine hydrochloride (Anavex1-41). Further, note is made of tetrahydro-N,N-dimethyl-2,2-diphenyl-3-furanmethanamine hydrochloride (ANAVEX™2-73, AV2-73, or A2-73) in methods of treatment for neurodevelopmental disorders (U.S. Ser. No. 62/287,062).

Sigma-1 (σ1) receptors are small proteins located in the endoplasmic reticulum (ER), in the subregion contacting the mitochondria. They regulate NMDA receptors and have been reported as reducing mitochondrial dysfunction and oxidative stress. Reportedly, in the absence of Aβ aggregation, there is: i) neuronal coupling of lactate with diurnal Aβ oscillations; and, ii) glutamate supply back to neurons by the astrocytes, as a mechanism involved in the fine tuning of sleep oscillations. According to the "astrocyte-neuron-lactate shuttle hypothesis" (Petit et al., "Regulation of neuron-astrocyte metabolic coupling across the sleep-wake cycle," Neurosci 323:135-156 (2016)), lactate coupling with diurnal oscillation of Aβ could be lost after Aβ aggregation, as astrocytes responsible for clearing Aβ become mobilized moving toward plaques. This is believed to initiate a positive feedback loop in which astrocytes no longer metabolize Aβ or remove glutamate from nearby neurons, leading to further aggregation of Aβ and to neuronal injury due to glutamate excitoxicity. In parallel, this is believed to increase sleep fragmentation due to increased hyperexcitability of glutamate neurons and to loss of synchronized activation of neuronal columns during sleep.

Literature reports evidence linking high blood pressure to increased risk of cognitive decline and dementia. Antihypertensive medications reportedly protect the brain from AD, Østergaard et al., "Associations between Potentially Modifiable Risk Factors and Alzheimer Disease: A Mendelian Randomization Study," PLOS Medicine (Jun. 16, 2015 https://doi.org/10.1371/journal.pmed.1001841).

Note is made of the following publications, the teachings of which are incorporated herein by reference in their entirety as are all publications cited herein):

U.S. Ser. No. 13/940,352 (Vamvakides et al.), PCT/US16/42937, PCT/US16/42949 and PCT/US16/42958.

Zadnys et al., "Sleep Disturbances in the Elderly," Psychiatr Clin North Am, 2015 December; 38(4):723-41:

Khalsa, "Stress, Meditation, and Alzheimer's Disease Prevention: Where The Evidence Stands," J Alzheimers Dis. 2015; 48(1):1-12;

Liu et al, "Pharmacological management of agitation and aggression in Alzheimer's Disease: a review of current and novel treatments," Curr Alzheimer Res. 2016 May 2;

Kuiper et al., "Comparison of cognitive functioning as measured by the Ruff Figural Fluency Test and the CogState computerized battery within the LifeLines Cohort Study," BMC Psychol. 2017 May 12; 5(1):15, doi: 10.1186/s40359-017-0185-0;

Karmail et al., "Global Risk Assessment to Guide Blood Pressure Management in Cardiovascular Disease Prevention," Hypertension, 2017; 69:e2-e9 (https://doi.org/10.1161/HYPERTENSIONAHA.116.08249);

Darby et al., "Intraindividual cognitive decline using a brief computerized cognitive screening test," Alzheimer's and Dementia, 8(2), 95-104 (2012). doi:10.1016/j.jalz.2010.12.009

Maruff et al., "Clinical utility of the Cogstate brief battery in identifying cognitive impairment in mild cognitive impairment and Alzheimer's disease." BMC Pharmacology & Toxicology, 1:30 (2013)

A. J Larner, Cognitive Screening Instruments: A Practical Approach, Springer; 2nd ed. 2017 edition (2016).

SUMMARY OF THE INVENTION

This invention encompasses a method for treating insomnia, anxiety, or agitation in a subject in need of such therapy. Particular note is made of subjects suffering from Alzheimer's disease. The method comprises the step of administering to the subject pharmaceutically effective amount of a pharmaceutical selected from the group consisting of Anavex™2-73 (also termed A2-73), A1-41 or A19-144, and optionally as a dosage form comprising a pharmaceutically acceptable carrier. The method of administering is selected from the group consisting of oral administration, subcutaneous injection, intravenous injection, intraocular injection, intradermal injection, intramuscular injection, intraperitoneal injection, intratracheal administration, inhalation, intranasal administration, sublingual administration, buccal administration, rectal administration, vaginal administration, or topical administration.

The method contemplates a pharmaceutically effective amount is from about 10 mg to about 100 mg per day or more. Particular reference is made to a daily pharmaceutically effective amount of from about 10 mg to about 50 mg, and particularly from about 20 mg to about 30 mg.

The practice of the method draws particular attention to the use of A2-73, administering by oral dosing and administering is daily, every other day, or for about 10 or more days out of 30 days. Chronic dosing is contemplated.

Further contemplated is a method for treating insomnia, anxiety, or agitation in a subject in need of such therapy and further exhibiting systolic hypertension, comprising the step of administering to the subject pharmaceutically effective amount of a pharmaceutical selected from the group consisting of A2-73, A1-41 or A19-144.

DETAILED DESCRIPTION OF THE INVENTION

Without being bound by any particular theory, it is believed that that ANAVEX 2-73 as well as A1-41 and A19-144 reduce glutamate toxicity, oxidative stress and consequently improve sleep efficiency through σ1 agonism, and improved REM sleep duration and sleep efficiency though $M_{1-2}$ muscarinic agonism. In a phase-2A trial performed on a group of 30 community-dwelling mild AD patients with a DSM-5 diagnosis of insomnia dosing with ANAVEX 2-73 (a sigma-1 and muscarinic receptor agonist), the patients showed marked insomnia improvements at 12 weeks.

A2-73 is a useful therapeutic in the treatment of humans suffering from insomnia, anxiety or agitation. Particular attention is drawn to oral daily doses of from about 10 mg to about 50 mg and up to 100 mg, with particular reference to about 20 to 30 mg. Attention is also directed to A1-41 and A19-144 as similarly useful therapeutics in insomnia, anxiety or agitation.

This invention will be better understood with reference to the following definitions:

The term "pharmaceutically effective amount" as used herein as to insomnia refers to a dose or quantity that causes improvement in at least one objective or subjective sleep parameter deficiency associated with insomnia including, but not limited to: difficulty falling asleep; difficulty maintaining sleep; decrease in total sleep time; persistent waking after sleep onset (WASO); and poor sleep quality.

Although the present invention calls for methods of treating insomnia, some primary sleep disorders, such as circadian rhythm disorders, advanced sleep phase disorder also termed sleep onset insomnia, mid-nocturnal insomnia, early morning insomnia, hyper insomnia, trouble staying asleep, jet lag, narcolepsy, non-24-hour sleep-wake syndrome, include insomnia as a component of the disorder. Thus, the term "insomnia" should be understood to also include the insomnia component of these disorders.

Aβ—Amyloid beta is abbreviated as Aβ.

AD—Alzheimer's disease is abbreviated as AD.

ADCS-ADL—Alzheimer's Disease Cooperative Study Activities of Daily Living Inventory is abbreviated as ADCS-ADL.

Cogstate tasks—Cogstate tasks refers to Cogstate cognitive tests (Cogstate Alzheimer's Battery) using visual and verbal stimuli to ensure assessment. These tests assess cognitive function in adults with mild cognitive impairment and clinically-diagnosed Alzheimer's disease. The test is culture-neutral and not limited by a subject or participant's level of education. A Cogstate battery comprises a number of individual tests—each designed to test a specific area of cognition. When a number of these individual tests are put together to form a test battery, a more complete picture of a person's cognitive state can be defined.

DPZ—Donepezil is abbreviated as DPZ.

EEG/ERP—EEG/ERP is a reference to ERP measured via EEG.

ERP—Event-related potential is abbreviated as ERP.

HAM-D—Hamilton Depression Rating Scale is abbreviated as HAM-D.

MCI—Mild cognitive impairment is abbreviated as MCI.

MMSE—MMSE refers to the Mini-Mental State Examination (MMSE) or Folstein test. This test is a 30-point questionnaire that is used extensively in clinical and research settings to measure cognitive impairment.

SWS—Slow-wave sleep is abbreviated as SWS.

WASO.—Waking after sleep onset is abbreviated WASO.

An event-related potential (ERP) is the measured brain response that is the direct result of a specific sensory, cognitive, or motor event. More formally, it is any stereotyped electrophysiological response to a stimulus. The study of the brain in this way provides a noninvasive means of evaluating brain functioning. ERPs are measured by means of electroencephalography (EEG).

The safety and efficacy of A2-73 has been studied Phase 2a Study in mild-moderate Alzheimer's disease patients. A study of 32 patients with mild-to-moderate Alzheimer's disease (AD) demonstrated a favorable safety and tolerability/risk profile for A2-73. Without being bound by any particular theory, it is believed that A2-73 activates the stress-reducing and survival protein, the Sigma-1 receptor.

Efficacy data is presented through 31 week from the randomized (into different treatment regimens) open-label study with ANAVEX 2-73 oral daily dosing ranging from 10 mg to 50 mg. The data establish a method for treating insomnia, anxiety, or agitation in a subject. Efficacy extends to daily doses of up to about 100 mg of A2-72, A1-41 or A19-144. Note is made of doses of A2-73, A1-41 or A19-144 of about 10 mg to about 30 mg, about 20 mg to about 40 mg, about 50 mg to about 80 mg. Oral dosing daily or every other day is contemplated.

Particular efficacy data measurements addressed cognition and function. Cognitive measures include MMSE and Cogstate battery. Functional measures were ADCS-ADL. Supportive Biomarker Measurements include ERP (P300): fundamental measures of synaptic network performance and target engagement. ERP target detection task measures is a direct measure of attention, speed of brain processing, and simple functional performance.

Figure 1:
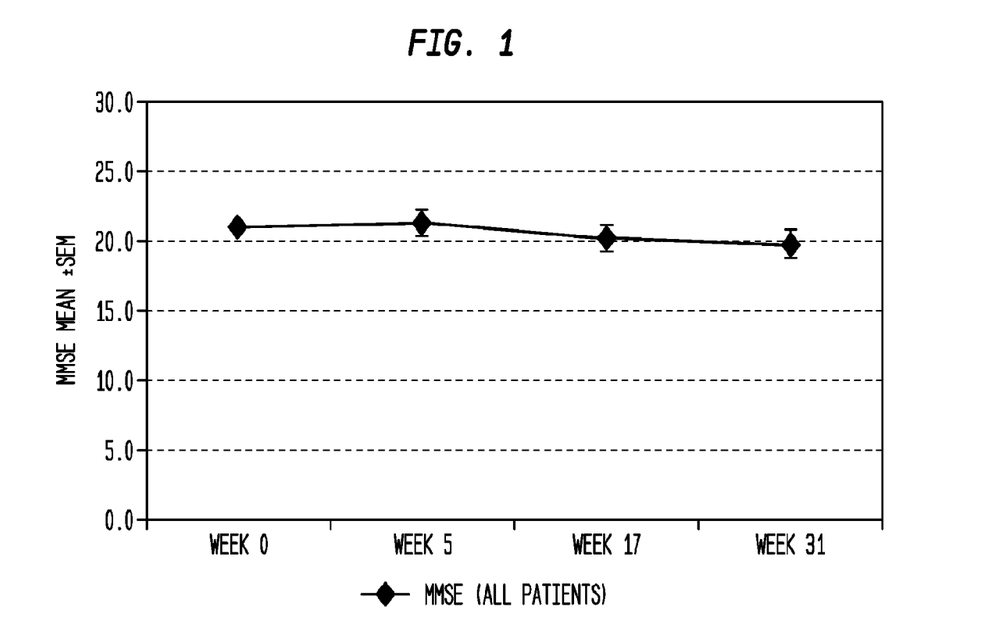
FIG. 1 presents MMSE mean scores over 31 weeks of A2-73 dosing.

FIG. 1 presents MMSE mean scores over 31 weeks. Statistical analysis of MMSE revealed no other grouping factors (sex, ApoE4, age, donepezil, baseline value) influencing the analysis. Statistical analyses also revealed overall A-MMSE-scores maintained at the same level and effects were confirmed with Bayesian inference calculations. In a disease state where progression is invariable over time, a stable MMSE score represents a positive outcome treating insomnia, anxiety, or agitation.

Figure 2:
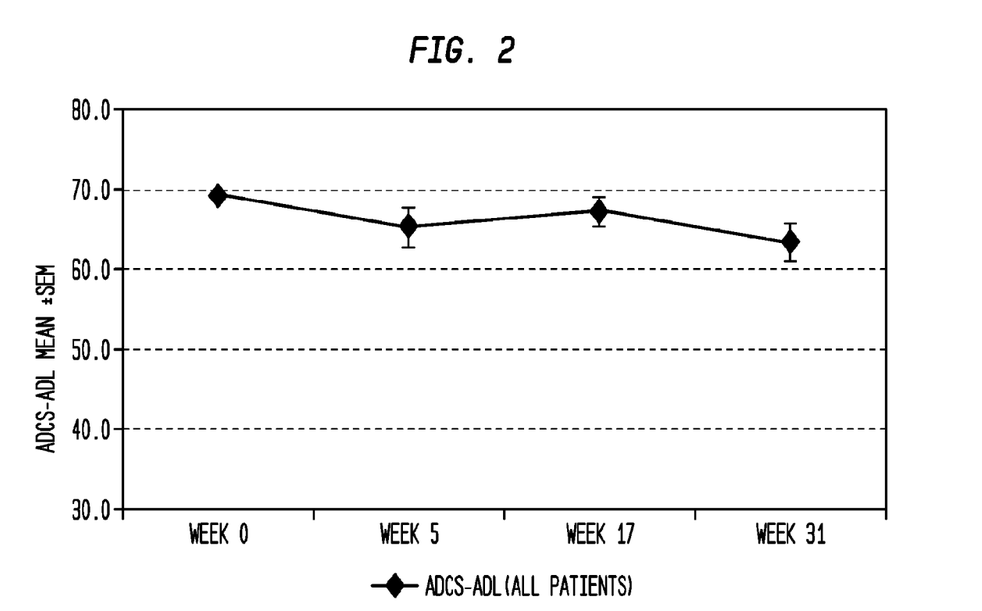
FIG. 2 is a graphic representation of ADCS-ADL data over 31 weeks of A2-73 dosing.

FIG. 2 is a graphic presentation of ADCS-ADL data. Data speaks to a quality of life score ADCS-ADL (Activities of Daily Living), here, as maintained through week 31 of A2-73 dosing. ADCS-ADL-Δ-scores were also maintained at a constant level through week 31 and effects were confirmed with Bayesian inference calculations. Again, in a disease state where progression is invariable over time as is the case here, a stable ADCS-ADL score is considered a positive outcome.

Figure 3:
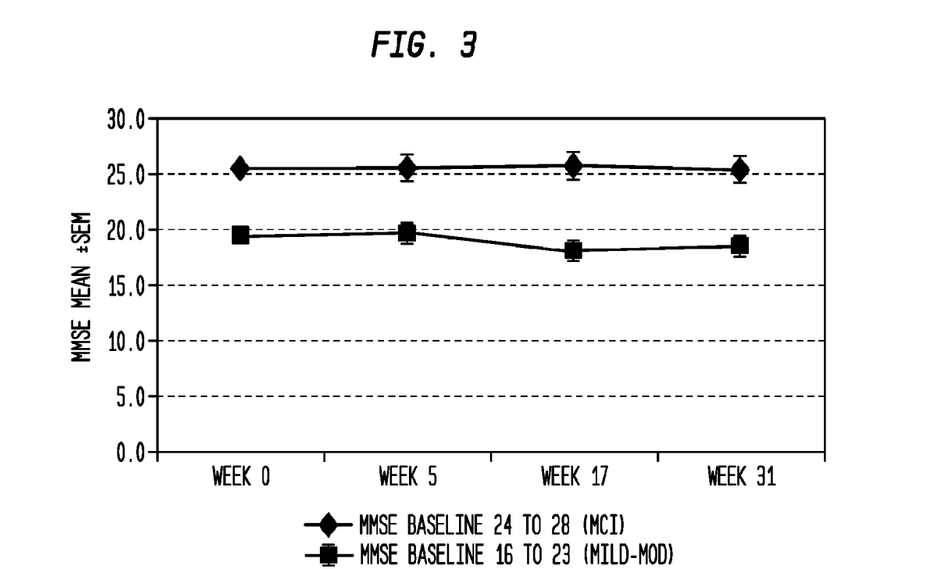
FIG. 3 presents data on both MMSE MCI and Mild-to-Moderate Patients over 31 weeks of A2-73 dosing.

FIG. 3 presents data on both MMSE MCI and Mild-to-Moderate Patients. Given unequal sample size, data after stratification are considered preliminary. Similar effect are noted on MMSE in both MCI and Mild-to-Moderate AD patients.

Figure 4:
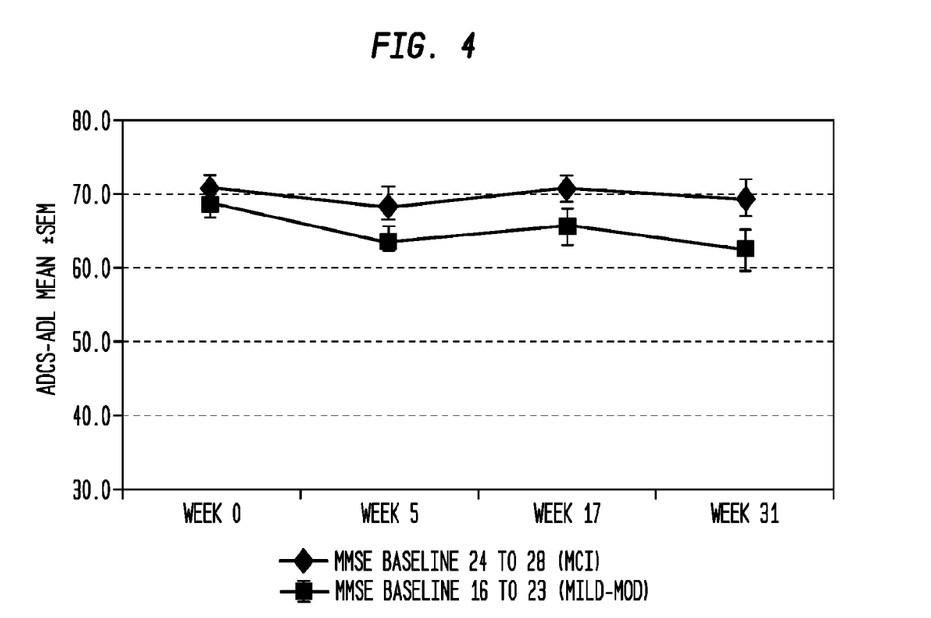
FIG. 4 presents data on both ADCS-ADL MCI and Mild-to-Moderate Patients over 31 weeks of A2-73 dosing.

FIG. 4 presents data on both ADCS-ADL MCI and Mild-to-Moderate Patients. Similar ADCS-ADL score effect between MCI and Mild-to-Moderate AD patients are noted.

Figure 5:
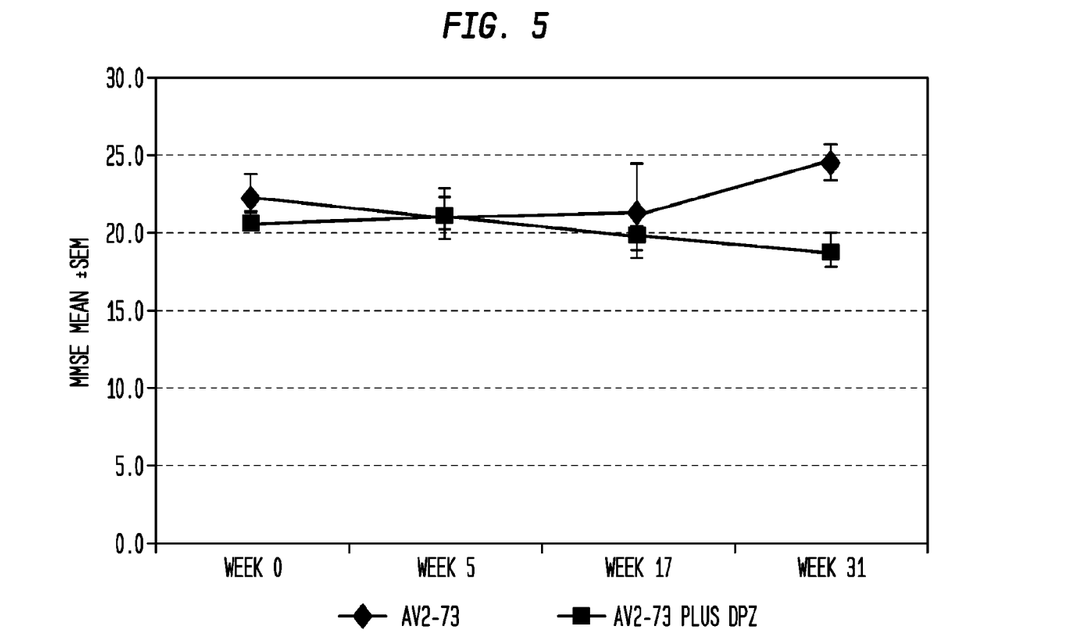
FIG. 5 presents data on MMSE ANAVEX 2-73 Alone vs with Donepezil over 31 weeks.

FIG. 5 presents data on MMSE ANAVEX 2-73 Alone vs A2-73 in combination with donepezil. Similar MMSE score effect and no notable difference between exploratory analysis of ANAVEX 2-73 alone and ANAVEX 2-73 with DPZ are noted.

Figure 6:
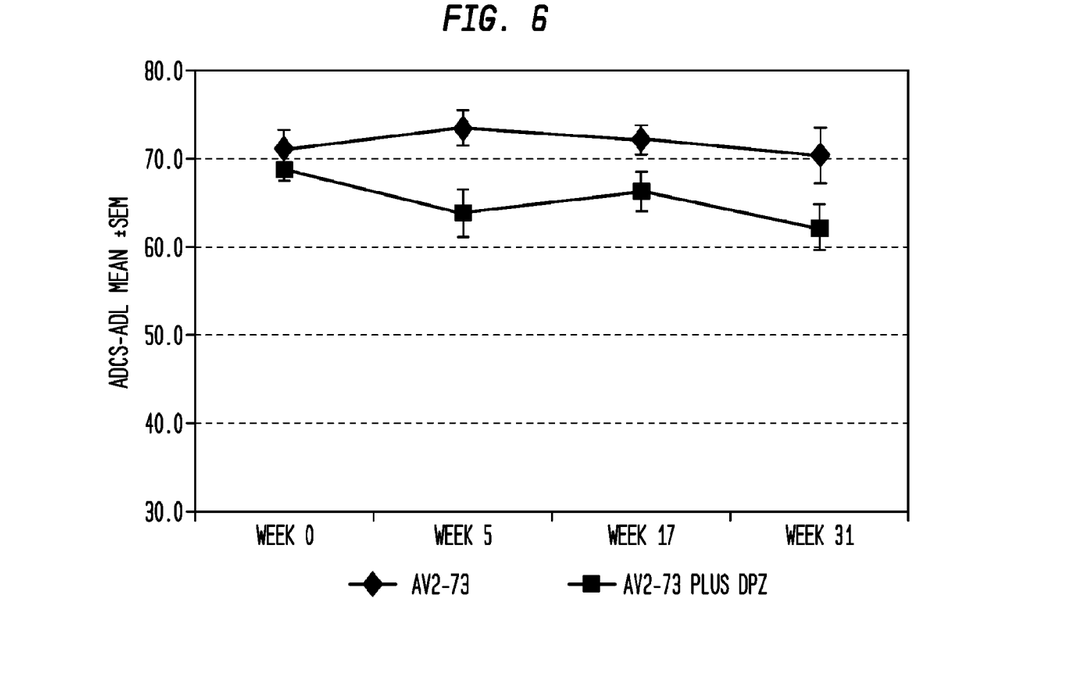
FIG. 6 presents data on ADCS-ADL ANAVEX 2-73 Alone vs with Donepezil over 31 weeks.

FIG. 6 presents data on ADCS-ADL ANAVEX 2-73 Alone vs A2-73 in combination with donepezil. Similar ADCS-ADL score and no notable difference between exploratory analysis of ANAVEX 2-73 alone and ANAVEX 2-73 with DPZ are noted.

Figure 7:
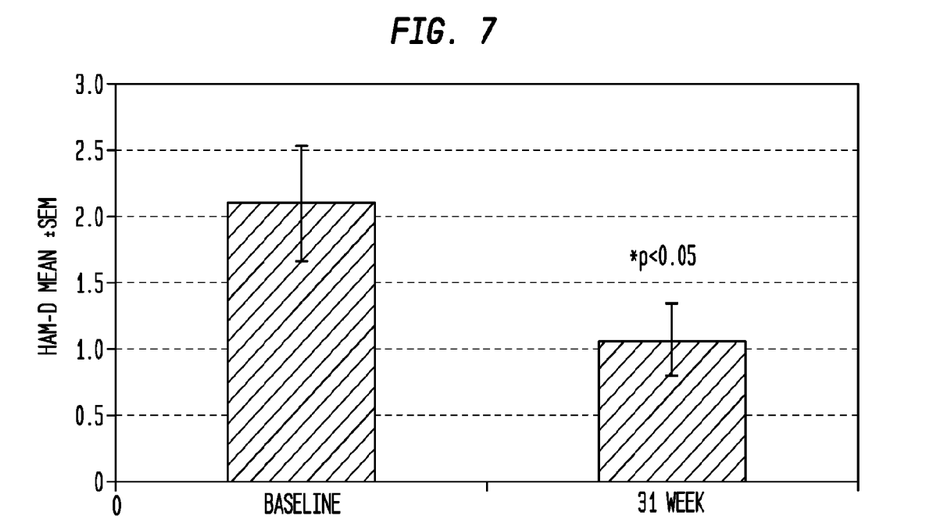
FIG. 7 is a graph of ANAVEX 2-73 treatment demonstrating reduction in overall Hamilton Depression Rating Scale (HAM-D) after 31 weeks.

FIG. 7 of ANAVEX 2-73 treatment demonstrates reduction in overall Hamilton Depression Rating Scale (HAM-D) after 31 weeks of dosing with A2-73. This is consistent with Table 1 showing a reduction in insomnia, anxiety, and other symptoms.

TABLE 1

| Improved Items of HAM-D | Scored Improvement Count | in [%] |
| --- | --- | --- |
| Insomnia | 8 | 29% |
| Work and activities | 6 | 21% |
| Anxiety (psychic and somatic) | 5 | 18% |
| Agitation | 4 | 14% |

TABLE 1-continued

| Improved Items of HAM-D | Scored Improvement Count | in [%] |
| --- | --- | --- |
| Depressed | 4 | 14% |
| Insight | 3 | 11% |
| Hypochondriasis | 2 | 7% |
| Loss of libido or other genital symptoms | 2 | 7% |
| Guilt | 1 | 4% |
| Total | 28 | |

The data of Table 1 is from an open-label, clinical trial, performed on a group of 30 mild-to-moderate AD patients (MMSE range 16-23, 40% female) on donepezil treatment, with ANAVEX 2-73. Patients showed marked improvements on subjective reports of insomnia (the sleep items of the Hamilton Depression Rating scale, HAM-D) (see also, Table 2) from baseline to week 12 (t=4.2; p<0.05). Changes in other behavioral items were not statistically significant. Anavex 2-73 at 30 mg was well tolerated with the most common adverse events (AEs) being mild dizziness (5%) and headache (10%), and no significant changes in clinical labs and EKGs.

TABLE 2

| Insomnia HAM-D | Baseline Mean ± SD | Day 13 Mean ± SD | Week 12/26 Mean ± SD |
| --- | --- | --- | --- |
| Q4 Initial Insomnia | 2 ± 0.0 | 2 ± 0.0 | 0.0 ± 0.0 |
| Q5 Middle Insomnia | 1.5 ± 0.7 | 1.0 ± 1.4 | 0.0 ± 0.0 |
| Q6 Late Insomnia | 1.6 ± 0.5 | 0.0 ± 0.0 | 0.0 ± 0.0 |

Q4. Insomnia Early

0=No difficulty in falling asleep

1=Complains of occasional difficulty in falling asleep—i.e., more than ½ hour

2=Complains of nightly difficulty falling asleep

Q5. Insomnia Middle

0=No difficulty

1=Patient complains of being restless and disturbed in the night

2=Waking during the night—any getting out of bade rates 2 (except for the purposes of voiding)

Q6. Insomnia late

0=No difficulty

1=Waking in the early hour of the morning but goes back to sleep

2=Unable to fall asleep again if patient gets out of bed

Figure 8:
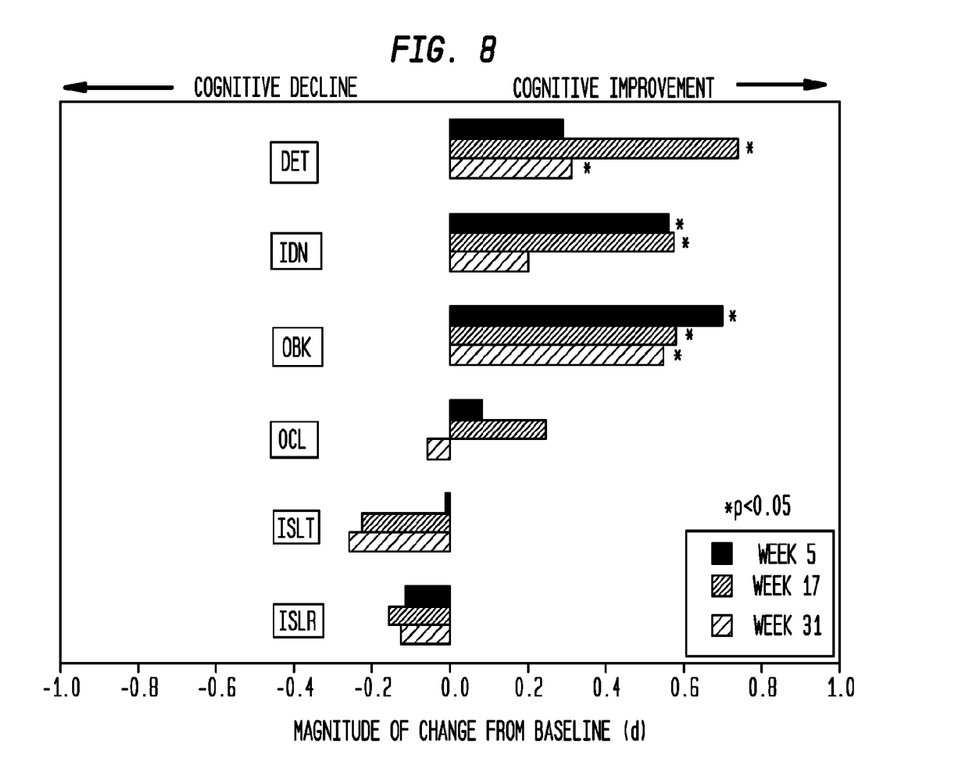
FIG. 8 is a chart of Anavex 2-73 improving components of cogstate tasks.

FIG. 8 is a chart of Anavex 2-73 improving components of cogstate tasks. ANAVEX 2-73 treatment demonstrates reduction in overall Hamilton Depression Rating Scale (HAM-D) after 31 weeks of treatment. Over 31 weeks of treatment, ANAVEX 2-73 was associated with a sustained benefit in psychomotor function, attention and working memory. The specificity and consistency of these benefits establish that ANAVEX 2-73 sustains activation of attentional and working memory functions with repeated dosing in Alzheimer's disease.

Figure 9:
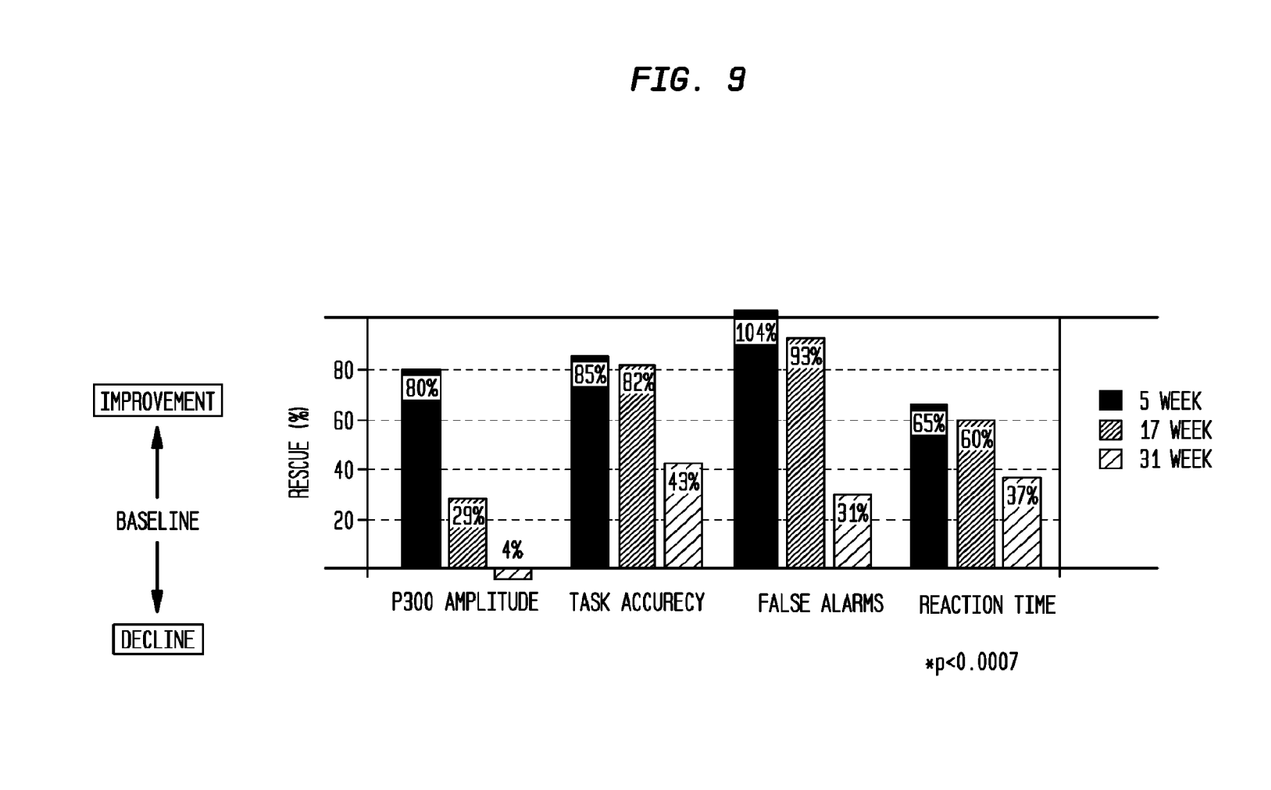
FIG. 9 presents EEG/ERP data showing ANAVEX 2-73 Rescues Cognitive Effects on a Cellular Level.

Table 3 and FIG. 9 presents EEG/ERP data that ANAVEX 2-73 Rescues Cognitive Effects on a Cellular Level on the subjects of the Phase 2a study.

TABLE 3

|  | Baseline | 5 Week | 17 Week | 31 Week | Healthy Control |
|---|---|---|---|---|---|
| P300 Amplitude (μV) | 5.99 ± 0.58 | 7.09 ± 0.72 | 6.38 ± 0.61 | 5.93 ± 0.77 | 7.36 ± 0.39 |
| Task Accuracy (%) | 83.8 ± 3.8 | 92.6 ± 2.4 | 92.2 ± 3.9 | 88.1 ± 4.4 | 94.1 ± 1.1 |
| False Alarms (%) | 3.4 ± 1.0 | 1.0 ± 0.5 | 1.2 ± 0.9 | 2.6 ± 1.2 | 1.1 ± 0.2 |
| Reaction Time (ms) | 559.0 ± 24.0 | 492.6 ± 23.8 | 498.8 ± 24.8 | 521.8 ± 28.1 | 458.6 ± 11.4 |

Data are mean ± SEM*p > 0.0007

ANAVEX 2-73 effect on synaptic networks and effect on cognition and behavior at daily doses of 10 mg-50 mg is shown. ERP peak measures (P300) are shown. The P300 (P3) wave is an event related potential (ERP) component elicited in the process of decision making. It is considered to be an endogenous potential, as its occurrence links not to the physical attributes of a stimulus, but to a person's reaction to it. More specifically, the P300 is thought to reflect processes involved in stimulus evaluation or categorization. ERP target detection task is a direct measure of attention, speed of brain. processing, and simple behavioral performance. Psychometric measures (Cogstate) cognitive measures: Detection: processing speed (psychomotor function), Identification: reaction time (attention), One Back: working memory (cognition), One Card Learning: visual learning (visual memory), ISLT: verbal learning, ISLT-delay: verbal memory. Psychometric measures (MMSE): cognitive measures. Behavioral measures (ADCS-ADL): behavioral measures. Notably, FIG. 9 shows that all tested areas exhibited improvement at 5 weeks as compared with the starting baseline (hence, absent expected decline).

Oral daily doses of ANAVEX 2-73 ranging from 10 mg to 50 mg exhibit a converging and consistent response for all measurements (MMSE, ADCS-ADL, Cogstate, EEG/ERP) throughout 31 weeks (7 months) of ANAVEX 2-73 treatment. Patient retention rate at week 31 was 84%. Treatment of ANAVEX 2-73 and related drugs demonstrates reduction in overall HAM-D score after 31 weeks, notably through reductions in insomnia, anxiety and agitation. Seventeen week data as well as 31 week data of all available patients demonstrate that ANAVEX 2-73 preserves average MMSE and ADCS-ADL scores across the entire patient group. In a disease state where progression is invariable over time, a stable MMSE and ADCS-ADL score is considered a positive outcome. When the group is tentatively stratified into mild to moderate and MCI (mild cognitive impaired) AD patients, no significant difference was observed within the MMSE or the ADCS-ADL score, respectively. Likewise, when tentatively stratified between ANAVEX 2-73 alone and ANAVEX 2-73 PLUS donepezil administration, no significant difference was observed within the MMSE or the ADCS-ADL score, respectively. For cognitive assessment using the Cogstate test batteries, ANAVEX 2-73 continues to show benefits over baseline at 17 weeks and 31 weeks. ANAVEX 2-73 related improvement in psychomotor function, attention and working memory are preserved through 17 weeks and 31 weeks of treatment. Repeated-measures ANOVA reveals that Cogstate values maintained the baseline values through week 31.

An additional benefit of the therapeutic regimen disclosed herein is the beneficial control of systolic blood pressure in AD subjects taking daily oral dosages of A2-73 of from about 10 mg to about 50 mg. Systolic blood pressure was monitored over the first 25 days of dosing. A1-41 and A19-144 are similarly useful therapeutics.

Table 3 shows that A2-73 therapy significantly reduced systolic blood pressure in hypertensive subjects with greater reduction for increasingly hypertensive subjects. And further surprisingly, systolic blood pressure rose is subjects that exhibited high-normal systolic blood pressure.

TABLE 3

| Baseline Hypertension Classification [mm Hg] | No. Subjects (beginning) | Baseline Mean systolic BP [mm Hg] ± SD | No. Subjects Day 25 | Day 25 - Mean systolic BP [mm Hg] ± SD | Change |
|---|---|---|---|---|---|
| <120 | 3 | 115 ± 2 | 2 | 123 ± 11 | 8 |
| Pre Hypetension 120-139 | 12 | 131 ± 6 | 12 | 122 ± 15 | −9 |
| Hypertension Stage 1: 140-159 | 10 | 145 ± 3 | 10 | 129 ± 12 | −16 |
| Hypertension Stage 2: 160-179 | 5 | 170 ± 8 | 5 | 148 ± 19 | −22 |
| Hypertensive crisis >180 | 2 | 185 ± 0 | 2 | 159 ± 43 | −27 |

Example 1

Maintenance Insomnia Therapy

A 48 year old female presents as suffering from maintenance insomnia for one year. She is started on oral A2-73 at 10 mg/day. Follow up at 30 days of daily dosing reveals she is sleeping well. She is currently maintained on 10 mg of A2-73 and is sleeping well.

Example 2

Anxiety Therapy

A 51 year old female presents with anxiety of three years' duration. She is administered A2-73 at 20 mg oral per day every other day. Resolution of the anxiety is noted after two days of dosing. She is maintained on this dosing schedule for 60 days.

Example 3

Agitation Therapy

The patient is a 29-year-old male exhibiting agitation. He is treated with 30 mg A2-73 oral daily for 30 days. Clinical evaluation reveals normal affect without agitation, depression, anxiety, or substance use. He is currently maintained at that dosage and is not anxious.

Example 4

Maintenance Insomnia Therapy

A 68 year old female presents with MCI and reports maintenance insomnia for one year. She is started on oral A1-41 at 10 mg/day. Follow up at 30 days of daily dosing reveals she is sleeping well. She is currently maintained on 10 mg of A1-41 and is sleeping well.

Example 5

Anxiety Therapy

The patient is a 52 year old female with diagnosed AD and reported anxiety of three years' duration. She is administered A19-144 at 20 mg oral per day every day for 90 days. Resolution of the anxiety is noted after two days of dosing. She is chronically maintained on this dosing schedule.

Example 6

Maintenance Insomnia Therapy in MIC

A 66 year old male diagnosed with mild cognitive impairment presents as suffering from maintenance insomnia for one year. He is started on oral A2-73 at 50 mg/day. Follow up at 30 days of daily dosing reveals he is sleeping well. He is currently maintained on 50 mg of A2-73 daily and is sleeping well.

Example 7

Maintenance Insomnia Therapy in Alzheimer's Disease Related Insomnia and Agitation A 72 year old male diagnosed with Alzheimer's disease presents with insomnia/WASO and agitation and a systolic blood pressure of 145 mm Hg. He is started on oral A2-73 at 30 mg/day. Follow up at 30 days of daily dosing reveals he is sleeping well through the night and not waking up repeatedly and his systolic BP is 129. He is also less agitated. His results on all cognitive tests and HAM-D improve. He is currently maintained on 30 mg of A2-73 daily.

Example 8

Maintenance Insomnia Therapy in Alzheimer's Disease Related Insomnia and Agitation A 72 year old male diagnosed with Alzheimer's disease presents with insomnia/WASO and agitation. He is started on oral A2-73 at 100 mg/day. Follow up at 30 days of daily dosing reveals he is sleeping well through the night and not waking up repeatedly. He is also less agitated. His results on all cognitive tests and HAM-D improve. He is currently maintained on 100 mg of A2-73 every other day.

Example 9

Maintenance Insomnia Therapy in Alzheimer's Disease Related Insomnia and Agitation A 77 year old male diagnosed with Alzheimer's disease presents with insomnia/WASO and agitation. He is started on oral A19-144 at 50 mg/day. Follow up at 30 days of daily dosing reveals he is sleeping well through the night and not waking up repeatedly. He is also less agitated. His results on all cognitive tests and HAM-D improve. He is currently maintained on 50 mg of A19-144 daily.

Example 10

Maintenance Insomnia Therapy in Alzheimer's Disease Related Insomnia and Agitation A 77 year old male diagnosed with Alzheimer's disease presents with insomnia/WASO and agitation. He is started on oral A1-41 at 30 mg/day. Follow up at 60 days of daily dosing reveals he is sleeping well through the night and not waking up repeatedly. He is also less agitated. His results on all cognitive tests and HAM-D improve. He is currently maintained on 30 mg of A1-41 daily.

The pharmacologically active compositions of this invention can be processed in accordance with conventional methods of Gaenlic pharmacy to produce medicinal agents for administration to subjects, e.g., mammals including humans.

The compositions of this invention individually or in combination are employed in admixture with conventional excipients, i.e., pharmaceutically acceptable organic or inorganic carrier substances suitable for parenteral, enteral (e.g., oral or inhalation) or topical application which do not deleteriously react with the active compositions. Suitable pharmaceutically acceptable carriers include but are not limited to water, salt solutions, alcohols, gum arabic, vegetable oils, benzyl alcohols, polyethylene glycols, gelatin, carbohydrates such as lactose, amylose or starch, magnesium stearate, talc, titanium dioxide, silicic acid, viscous paraffin, perfume oil, fatty acid esters, hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compositions. They can also be combined where desired with other active agents, e.g., vitamins.

In some embodiments of the present invention, dosage forms include instructions for the use of such compositions.

For parenteral application, particularly suitable are injectable, sterile solutions, preferably oily or aqueous solutions, as well as suspensions, emulsions, or implants, including suppositories. Ampules, vials, and injector cartridges are convenient unit dosages.

The invention claimed is:
1. A method of treating insomnia, or anxiety, in a subject in need thereof, comprising the step of administering to the subject a pharmaceutically effective amount of a compound selected from the group consisting of tetrahydro-N,N-dimethyl-2,2-diphenyl-3-furanmethanamine hydrochloride (A2-73),
tetrahydro-N,N-dimethyl-5,5-diphenyl-3-furanmethanamine hydrochloride (A1-41), and
1-(2,2-diphenyltetrahydrofuran-3-yl)-N-methylmethanamine hydrochloride (A19-144).

2. The method of claim 1, wherein the administering comprises a route of administration selected from the group consisting of oral administration, subcutaneous injection, intravenous injection, intraocular injection, intradermal injection, intramuscular injection, intraperitoneal injection, intratracheal administration, inhalation, intranasal administration, sublingual administration, buccal administration, rectal administration, vaginal administration, and topical administration.

3. The method of claim 1, wherein said pharmaceutically effective amount is from about 10 mg to about 100 mg per day.

4. The method of claim 3, wherein said pharmaceutically effective amount is from about 10 mg to about 50 mg per day.

5. The method of claim 4, wherein said pharmaceutically effective amount is from about 20 mg to about 30 mg per day.

6. The method of claim 1, wherein said pharmaceutical is A2-73.

7. The method of claim 1, wherein said administering is daily.

8. The method of claim 1 wherein said administration is for about 10 or more days out of 30 days.

9. The method of claim 1, wherein said pharmaceutical is in an oral dosage form comprising a pharmaceutically acceptable carrier.

10. The method of claim 1, wherein the subject further exhibits systolic hypertension.

\* \* \* \* \*